United States Patent [19]
Gehringer et al.

[11] Patent Number: 5,648,472
[45] Date of Patent: Jul. 15, 1997

[54] PROCESS FOR PREPARING VIRUS-INACTIVATED IMMUNOGLOBULIN SOLUTIONS

[75] Inventors: Werner Gehringer, Vienna, Austria; Patrick Selosse, Bordeaux, France

[73] Assignee: Octapharma AG, Glarus, Switzerland

[21] Appl. No.: 329,684

[22] Filed: Oct. 26, 1994

Related U.S. Application Data

[63] Continuation of Ser. No. 923,446, Aug. 3, 1992, abandoned.

[30] Foreign Application Priority Data

Aug. 2, 1991 [DE] Germany .................. 41 25 625.5

[51] Int. Cl.⁶ .................. C07K 16/00; C07K 1/14; C07K 1/20
[52] U.S. Cl. .................. 530/412; 530/415; 530/416; 530/389.1; 530/390.1
[58] Field of Search .................. 530/412, 415, 530/416, 389.1, 390.1

[56] References Cited

U.S. PATENT DOCUMENTS

| | | | |
|---|---|---|---|
| 4,789,545 | 12/1988 | Woods et al. | 424/101 |
| 5,094,960 | 3/1992 | Bonomo | 436/178 |

FOREIGN PATENT DOCUMENTS

| | | |
|---|---|---|
| 0 058 993 | 9/1982 | European Pat. Off. . |
| 0073371 | 3/1983 | European Pat. Off. . |
| 0 099 445 | 2/1984 | European Pat. Off. . |
| 0 131 740 | 1/1985 | European Pat. Off. . |
| 0 239 859 | 10/1987 | European Pat. Off. . |

OTHER PUBLICATIONS

Prince et al., PNAS, USA, 85:6944, 1988, Failure. HIV.

*Primary Examiner*—Frank C. Eisenschenk
*Attorney, Agent, or Firm*—Jacobson, Price, Holman & Stern, PLLC

[57] ABSTRACT

This invention describes a process for preparing virus-inactivated immunoglobulin solutions suitable for intravenous application, characterized in that the immunoglobulin is treated with non-ionic surfactants which subsequently are removed by solid-phase extraction on hydrophobic materials.

9 Claims, No Drawings

PROCESS FOR PREPARING VIRUS-INACTIVATED IMMUNOGLOBULIN SOLUTIONS

This is a continuation of application Ser. No. 07/923,446, filed Aug. 3, 1992, now abandoned, which is abandoned upon the filing hereof.

This invention is directed to a process for preparing virus-inactivated immunoglobulin solutions suitable for intravenous injection.

Immunoglobulins are humoral glycoproteins which, in electrophoresis of plasma or serum proteins migrate with the so-called γ-fraction and, thus, were formerly referred to as γ-globulins.

Because of their high antibody content immunoglobulins are used in the prophylaxis and therapy of infections.

It is known to prepare immunoglobulins for both intramuscular and subcutaneous application. A frequently employed method of preparation is the so-called Cohn-Oncley fractionation, also referred to as 6/9 method [Cohn et al. J. Am. Chem. Soc. 68, 459 (1946); Oncley et al. J. Am. Chem. Soc. 71, 541 (1949)].

However, this method of preparation is disadvantageous in that it results in a highly viscous solution which is applicable only by intra-muscular and subcutaneous routes and has high antibody concentrations in relatively small volumes.

While the obtained product is stable at 4° C., proteolysis caused by plasmin contaminations may occur, however. Furthermore, IgA and IgG dimers may be present which, on application, may give rise to anaphylactic reactions in patients (Ullmann, encyclopedia of Industrial Chemistry 1989, A14, pp. 93, 94).

For this reason, intravenously applicable immunoglobulins have been developed which exhibit improved tolerance in the patient. They are prepared from the so-called fraction 3, or Cohn fraction 2 (Cohn et al., see above) at pH 4 using polyethyleneglycol, subsequent ethanol precipitation, ultrafiltration or diafiltration, and ion exchange chromatography. The immunoglobulin thus obtained is stabilized with mono- or disaccharides.

Such an improved process is described in EP 0,073,371.

Starting out from fraction 3 (Cohn et al., see above), ultrafiltration and diafiltration are conducted after dissolving and adjusting the pH value to pH 4. Subsequently, the filtrate obtained is concentrated to a protein content of 5% by weight, and the alcohol content is reduced to 8% by weight. Once the immunoglobulin solution thus obtained has been concentrated up to a protein content of 8%, a clear water-like solution having an ionic strength of 0.01 and a pH value of 4.2 is obtained. Using 10% by weight of maltose, the tonicity of the solution is adjusted at a protein content of 5% by weight. Subsequently, sterile filtration and lyophilization are effected. Prior to injection, the lyophilized material is dissolved in suitable media.

One major drawback of the immunoglobulins thus prepared for intravenous application is that prior to use, they must be dissolved in suitable media and can be stored in lyophilized form only.

Another drawback lies in the fact that in applying these immunoglobulins, viruses may be transferred to the patient since no virus inactivation occurs during the production process. Thus, hepatitis diseases and HIV infections have been reported after intravenous immunoglobulin administration (Ullmann's Encyclopedia of Ind. Chem., Vol. A14, 1989, pp. 102, 103).

Therefore, the technical problem of the invention was to develop a process for virus inactivation of intravenously injectable immunoglobulins resulting in a product wherein virus transfer to the patient during application does not occur, and which is stable to an extent that even without lyophilization, it can be prepared and stored directly as an injectable solution.

The technical problem of the invention is solved by a process, characterized in that the immunoglobulin is treated with non-ionic surfactants which subsequently are removed by solid-phase extraction on hydrophobic materials.

As the non-ionic surfactants, especially TNBP and/or TRITON×100 are used. Preferably, the pH value of the solution is from 5.0 to 5.5.

In a preferred embodiment, subsequent to treatment with non-ionic surfactants, an extraction is conducted using biologically compatible vegetable oils followed by removal thereof. As the vegetable oils, castor oil or soy bean oils are used preferably.

The subsequent solid-phase extraction is conducted in preferred fashion using octadecyl-derivatized materials also used in reversed-phase chromatography. In a particularly preferred embodiment, solid-phase extraction is effected by reversed-phase chromatography on octadecyl (C-18) resin.

Following solid-phase extraction, a disaccharide may be added to the final product for stabilization. The final solution then is subjected to single or multiple sterile filtration.

Furthermore, the immunoglobulin solution may be subjected to ultra- or diafiltration prior to virus inactivation and/or subsequent to sterile filtration.

In the following, the production process of the invention is described in detail. Initially, as is known from prior art, the so-called Cohn fraction II is dissolved in water until a completely clear solution is obtained. Then, the solution is adjusted to a pH value of from 4.0 to 5.0, preferably 4.5, and filtered to remove contaminations.

Subsequently, the solution is subjected to ultrafiltration, and the solution is pre-concentrated. The ultrafiltration exclusion limit is 30,000 Dalton. In this step, contaminations having low molecular weights are removed especially. Subsequently, a diafiltration is effected to remove ions, which is followed by the actual virus inactivation.

In doing this, the solution first is cooled down to from 4° to 8° C., and the pH value is adjusted to from 5.0 to 5.5, preferably 5.3. Then, non-ionic surfactants, preferably TNBP and/or Triton×100 are added, and this solution then is stirred for several hours. Subsequently, in a preferred embodiment, a vegetable oil extraction may be carried out. Here, 5% by weight of vegetable oil is added to the solution, the solution then is brought to room temperature and mixed with the vegetable oil by stirring. The subsequent phase separation is followed by filtration.

Then, the solution is applied to a C 18 column and is subjected to chromatography. Subsequent to chromatography, the pH value is adjusted to pH 4. Maltose is added to adjust tonicity. Subsequent to the following sterile filtration, stability of the solution thus obtained is tested by storing at 37° C. for at least 22 hours. If the solution shows turbidity, it cannot be used. If the solution does not show turbidity within this period of time, the pH value is adjusted to from 5.0 to 5.5, preferably 5.3, further ultrafiltration and diafiltration are carried out, and the solution thus obtained is adjusted to a protein content of 50 g/l by addition of maltose. Subsequently, another sterile filtration is carried out, and the solution is directly filled into infusion bottles.

The product thus obtained may be used for direct intravenous injection and is free of viruses.

The following embodiment is given to explain the process of the invention in more detail.

EXAMPLE

The Cohn fraction II is dissolved using a sixfold amount of water and stirred until a clear solution is obtained. Subsequently, the pH value is adjusted to 4.5 using 0.5N HCl. Next, this is followed by ultrafiltration wherein the solution is pre-concentrated to 90 g/l. A Novasette 30K membrane type is used. Subsequently, dilution is effected using a fivefold amount of water, and diafiltration is carried out at from 0.3 to 0.5 bars. Following this diafiltration, the diafiltered solution is adjusted to a protein content of 70 g/l. The solution is cooled down to 4° to 8° C. and adjusted to a pH value of 5.3, using 0.1N sodium hydroxide solution. Subsequently, 0.3% by weight of TNBP and 1% by weight of TRITON×100 (non-ionic surfactant) are added to the solution, followed by vigorous stirring. After about 4 hours at 4° to 8° C., 5% by weight of castor oil is added. Then, oil extraction is conducted at 15° C. The resulting phases are separated, followed by filtration using a Cuno sheet filter. Subsequently, the solution is applied to a C 18 column charged with octadecyl-derivatized materials. Then, the solution is adjusted to pH 4, and 100 g/l of maltose is added. This is followed by sterile filtration, and the sterile-filtered solution is stored at 37° C. for between 22 and 24 hours. The solution, being clear then, is adjusted to a pH value of 5.3 using 0.1N sodium hydroxide solution. Again, an ultrafiltration and a diafiltration are carried out followed by addition of maltose of 100 g/l and adjusting the solution to a protein content of 50 g/l. Subsequent to the following sterile filtration, the solution is filled into sterilized and siliconized 50 ml infusion bottles which are sealed with a stopper and tied up.

We claim:

1. A process for preparing an envelope virus-inactivated immunoglobulin solution suitable for intravenous application, comprising treating the immunoglobulin with TNBP and/or TRITON×100, followed by an extraction using biologically compatible vegetable oil, which TNBP and/or TRITON×100 and vegetable oil are subsequently removed by solid-phase extraction on hydrophobic materials.

2. The process according to claim 1, wherein the pH value of the solution is from 5.0 to 5.5.

3. The process according to claim 2, wherein castor oil and/or soy bean oil are used as vegetable oil.

4. The process according to claim 1, wherein the solid-phase extraction is carried out using octadecyl-derivatized materials also used for reverse-phase chromatography.

5. The process according to claim 1, wherein the solid-phase extraction is carried out using C 18 reversed-phase chromatography.

6. The process according to claim 1, wherein subsequent to solid-phase extraction, a disaccharide is added to the solution.

7. The process according to claim 1, wherein the final solution is subjected to a single or multiple sterile filtration.

8. The process according to claim 1, wherein the immunoglobulin solution is subjected to ultrafiltration and diafiltration prior to virus inactivation and/or subsequent to sterile filtration.

9. The process according to claim 1, wherein subsequent to solid-phase extraction or disaccharide addition, a stability test of the prepared solution is conducted.

* * * * *